United States Patent
Ginsberg et al.

(10) Patent No.: US 11,786,559 B2
(45) Date of Patent: Oct. 17, 2023

(54) BLOOD-BRAIN BARRIER COMPRISING ENGINEERED ENDOTHELIAL CELLS

(71) Applicant: ANGIOCRINE BIOSCIENCE, INC., San Diego, CA (US)

(72) Inventors: Michael Daniel Ginsberg, San Diego, CA (US); Daniel Joseph Nolan, Hawthorne, NY (US); Liang Qiang, Philadelphia, PA (US)

(*) Notice: Subject to any disclaimer, the term of this patent is extended or adjusted under 35 U.S.C. 154(b) by 894 days.

(21) Appl. No.: 16/332,634

(22) PCT Filed: Sep. 13, 2017

(86) PCT No.: PCT/US2017/051285
§ 371 (c)(1),
(2) Date: Mar. 12, 2019

(87) PCT Pub. No.: WO2018/052948
PCT Pub. Date: Mar. 22, 2018

(65) Prior Publication Data
US 2021/0283188 A1    Sep. 16, 2021

Related U.S. Application Data

(60) Provisional application No. 62/393,774, filed on Sep. 13, 2016.

(51) Int. Cl.
| | | |
|---|---|---|
| *C12N 5/079* | (2010.01) | |
| *C12N 5/071* | (2010.01) | |
| *C07K 14/005* | (2006.01) | |
| *C12N 15/86* | (2006.01) | |
| *A61K 35/44* | (2015.01) | |
| *A61K 35/13* | (2015.01) | |
| *A61K 35/30* | (2015.01) | |
| *A61L 27/38* | (2006.01) | |
| *C12N 5/09* | (2010.01) | |

(52) U.S. Cl.
CPC ............ *A61K 35/44* (2013.01); *A61K 35/13* (2013.01); *A61K 35/30* (2013.01); *A61L 27/3808* (2013.01); *A61L 27/3878* (2013.01); *A61L 27/3886* (2013.01); *C07K 14/005* (2013.01); *C12N 5/069* (2013.01); *C12N 5/0622* (2013.01); *C12N 5/0693* (2013.01); *C12N 5/0697* (2013.01); *C12N 15/86* (2013.01); *C12N 2502/086* (2013.01); *C12N 2502/28* (2013.01); *C12N 2710/10322* (2013.01)

(58) Field of Classification Search
None
See application file for complete search history.

(56) References Cited

U.S. PATENT DOCUMENTS

| | | |
|---|---|---|
| 5,260,210 A | 11/1993 | Rubin et al. |
| 6,093,553 A | 7/2000 | Yazdanian et al. |
| 6,852,533 B1 | 2/2005 | Rafii et al. |
| 7,396,680 B2 | 7/2008 | Shmelkov et al. |
| 8,084,254 B2 | 12/2011 | Couraud et al. |
| 8,293,495 B2 | 10/2012 | Shusta et al. |
| 8,465,732 B2 * | 6/2013 | Rafii ............ C12N 5/0606 435/325 |
| 9,637,723 B2 | 5/2017 | Rafii et al. |
| 10,113,149 B2 | 10/2018 | Sandler et al. |
| 10,877,026 B2 * | 12/2020 | Knipp ............ G01N 33/5014 |
| 10,946,066 B2 | 3/2021 | Rafii et al. |
| 10,947,500 B2 * | 3/2021 | Qiang ............ C12N 7/00 |
| 10,961,509 B2 | 3/2021 | Nolan et al. |
| 2005/0147643 A1 | 7/2005 | Hunter et al. |
| 2010/0273200 A1 | 10/2010 | Niwa et al. |
| 2013/0009511 A1 | 4/2013 | Smith et al. |
| 2013/0108548 A1 | 5/2013 | Vlieghe et al. |
| 2014/0045260 A1 | 2/2014 | Rafii et al. |
| 2017/0136068 A1 | 5/2017 | Kim et al. |
| 2017/0137781 A1 | 5/2017 | Qiang et al. |
| 2017/0241988 A1 | 8/2017 | Prehaud |
| 2017/0360988 A1 | 12/2017 | Ginsberg et al. |
| 2018/0214488 A1 | 8/2018 | Finnegan et al. |
| 2019/0127760 A1 | 5/2019 | Finnegan et al. |
| 2021/0030810 A1 | 2/2021 | Nolan et al. |
| 2022/0226391 A1 | 7/2022 | Wills et al. |

FOREIGN PATENT DOCUMENTS

| | | | |
|---|---|---|---|
| JP | 2001238681 A | 9/2001 | |
| WO | 1991005038 A1 | 4/1991 | |
| WO | 2011159572 A1 | 12/2011 | |
| WO | 2014186782 A1 | 11/2014 | |
| WO | WO 15/200897 | * 12/2015 | ............ C12N 5/073 |

OTHER PUBLICATIONS

Ma et al, Lab on a Chip, 2005, 5: 74-85. (Year: 2005).*
Abdullah Z, Rakkar K, Bath PM, Bayraktutan U. Inhibition of TNF-α protects in vitro brain barrier from ischaemic damage. Mol Cell Neurosci. Nov. 2015;69:65-79. doi: 10.1016/j.mcn.2015.11.003. Epub Nov. 9, 2015. PMID: 26546149.
Bohara M, Kambe Y, Nagayama T, Tokimura H, Arita K, Miyata A. C-type natriuretic peptide modulates permeability of the blood-brain barrier. J Cereb Blood Flow Metab. Apr. 2014;34(4):589-96. doi: 10.1038/jcbfm.2013.234. Epub Jan. 8, 2014. PMID: 24398935; PMCID: PMC3982079.
Gibson CL, Srivastava K, Sprigg N, Bath PM, Bayraktutan U. Inhibition of Rho-kinase protects cerebral barrier from ischaemia-evoked injury through modulations of endothelial cell oxidative stress and tight junctions. J Neurochem. Jun. 2014;129(5):816-26. doi: 10.1111/jnc.12681. Epub Mar. 1, 20148. PMID: 24528233.

(Continued)

*Primary Examiner* — Allison M Fox
(74) *Attorney, Agent, or Firm* — Grimes & Yvon LLP (57) ABSTRACT

The present invention relates, in part, to blood-brain barrier-like tissues that comprise engineered E40RF1+ endothelial cells, and to various compositions and methods useful for making and using such blood-brain barrier-like tissues—both in vitro and in vivo.

20 Claims, 8 Drawing Sheets

(56) References Cited

OTHER PUBLICATIONS

Grover A, Hirani A, Pathak Y, Sutariya V. Brain-targeted delivery of docetaxel by glutathione-coated nanoparticles for brain cancer. AAPS PharmSciTech. Dec. 2014;15(6):1562-8. doi: 10.1208/s12249-014-0165-0. Epub Aug. 19, 2014. PMID: 25134466; PMCID: PMC4245440.

Hanada S, Fujioka K, Inoue Y, Kanaya F, Manome Y, Yamamoto K. Cell-based in vitro blood-brain barrier model can rapidly evaluate nanoparticles' brain permeability in association with particle size and surface modification. Int J Mol Sci. Jan. 24, 2014;15(2):1812-25. doi: 10.3390/ijms15021812. PMID: 24469316; PMCID: PMC3958822.

Helms HC, Hersom M, Kuhlmann LB, Badolo L, Nielsen CU, Brodin B. An electrically tight in vitro blood-brain barrier model displays net brain-to-blood efflux of substrates for the ABC transporters, P-gp, Bcrp and Mrp-1. AAPS J. Sep. 2014;16(5):1046-55. doi: 10.1208/s12248-014-9628-1. Epub Jun. 17, 2014. PMID: 24934296; PMCID: PMC4147044.

Lippmann ES, Al-Ahmad A, Azarin SM, Palecek SP, Shusta EV. A retinoic acid-enhanced, multicellular human blood-brain barrier model derived from stem cell sources. Sci Rep. Feb. 24, 2014;4:4160. doi: 10.1038/srep04160. PMID: 24561821; PMCID: PMC3932448.

Novakova I, Subileau EA, Toegel S, Gruber D, Lachmann B, Urban E, Chesne C, Noe CR, Neuhaus W. Transport rankings of non-steroidal antiinflammatory drugs across blood-brain barrier in vitro models. PLoS One. Jan. 23, 2014;9(1):e86806. doi: 10.1371/journal.pone.0086806. PMID: 24466249; PMCID: PMC3900635.

Sajja RK, Prasad S, Cucullo L. Impact of altered glycaemia on blood-brain barrier endothelium: an in vitro study using the hCMEC/D3 cell line. Fluids Barriers CNS. Apr. 5, 2014;11(1):8. doi: 10.1186/2045-8118-11-8. PMID: 24708805; PMCID: PMC3985548.

Shao B, Bayraktutan U. Hyperglycaemia promotes human brain microvascular endothelial cell apoptosis via induction of protein kinase C-βI and prooxidant enzyme NADPH oxidase. Redox Biol. May 28, 2014;2:694-701. doi: 10.1016/j.redox.2014.05.005. PMID: 24936444; PMCID: PMC4052534.

Watson et al. Modelling the endothelial blood-CNS barriers: a method for the production of robust in vitro models of the rat blood-brain barrier and blood-spinal cord barrier. BMC Neuroscience. 2013, vol. 14, No. 59, pp. 1-21.

Benedicto et al. Concerted regulation of retinal pigment epithelium basement membrane and barrier function by angiocrine factors. Nat Commun. May 19, 2017; 8:15374.

Felner et al. Transport of paclitaxel (Taxol) across the blood-brain barrier in vitro and in vivo. The Journal of Clinical Investigation. Nov. 2002, vol. 110, No. 9; pp. 1309-1318.

Herrera et al. Sustained expression of vascular endothelial growth factor and angiopoietin-1 improves blood-spinal cord barrier integrity and functional recovery after spinal cord injury. Neurotrauma. Nov. 2010,27(11):2067-76.

Ma et al., 2004 An endothelial and astrocyte co-culture model of the blood-brain barrier utilizing an ultra-thin, nanofabricated silicon nitride membrane. The Royal Society of Chemistry. Oct. 14, 2004, Epub Oct. 14, 2004, vol. 5, No. 1; pp. 74-85.

O'Shea et al. "Adenoviral proteins mimic nutrient/growth signals to activate the mTOR pathway for viral replication", The EMBO Journal (2005) 24, 1211-1221.

Rauch, M.F., et al. Engineering angiogenesis following spinal cord injury: a coculture of neural progenitor and endothelial cells in a degradable polymer implant leads to an increase in vessel density and formation of the blood-spinal cord barrier. The European journal of neuroscience 29, 132-145 (2009).

Seandel et al.: "Generation of a functional and durable vascular niche by the adenoviral E4ORF1 gene"; Proceedings of the National Academy of Sciences (PNAS), 2008, vol. 105, No. 49. pp. 19288-19293.

Thai et al.: "Adenovirus E4ORF1-Induced MYC Activation Promotes Host Cell Anabolic Glucose Metabolism and Virus Replication", Cell Metabolism, vol. 19, No. 4, Apr. 1, 2014, pp. 694-70.

Zhang et al. "Adenovirus E4 Gene Promotes Selective Endothelial Cell Survival and Angiogenesis via Activation of the Vascular Endothelial-Cadherin/Akt Signaling Pathway"; The Journal of Biological Chemistry (2004) vol. 279, No. 12, pp. 11760-11766.

\* cited by examiner

BLOOD-BRAIN BARRIER COMPRISING ENGINEERED ENDOTHELIAL CELLS

CROSS-REFERENCE TO RELATED APPLICATIONS

This application claims the benefit of priority of U.S. Provisional Patent Application No. 62/393,774 filed on Sep. 13, 2016, the contents of which are hereby incorporated by reference in their entireties.

INCORPORATION BY REFERENCE

All publications, patent applications, patents, and other references mentioned herein are incorporated by reference in their entirety.

BACKGROUND OF THE INVENTION

The blood-brain barrier (BBB) separates circulating blood from the extracellular fluid and cells of the central nervous system (CNS). In vivo the BBB is formed by brain endothelial cells connected to one another by tight junctions, a basement membrane, and astrocytes—a type of glial cell. The BBB has a high electrical resistance and functions to restrict access of certain molecules and microorganisms (such as bacteria) to the CNS while allowing water, some gases, and some essential molecules (such as glucose and amino acids) to enter the CNS either by passive diffusion or by selective active transport.

While the barrier function of the BBB provides an essential safety mechanism in vivo—protecting the brain and spinal cord tissues—that same barrier function can pose a challenge to the development of therapeutic agents for treatment of the CNS—where the ability of drugs to cross the BBB would be beneficial. Conversely, when developing drugs that might have adverse effects on CNS tissues it can be desirable to develop agents that are not able to cross the BBB. Thus, there is a need in the art for model systems that can be used to study the ability of therapeutic agents to cross the BBB, and to screen for agents that have the desired BBB permeability, as well as to study other biological properties of the BBB in both normal and disease situations.

There is also a need in the art for means of treating, repairing, or replacing damage to the BBB that occurs in vivo—for example as the result of traumatic injury, disease, or infection.

The present invention is aimed at addressing all of these needs.

SUMMARY OF THE INVENTION

The present invention is based, in part, upon the surprising discovery that endothelial cells that have been engineered to express an adenovirus E4ORF1 protein can be used to generate a blood-brain barrier-like tissue that not only faithfully replicates many of the important characteristics of BBBs in vivo, but that, importantly, is superior in several important respects to BBB systems that utilize naïve (i.e. non-E4ORF1-expressing) endothelial cells. For example, and as described in more detail in the Examples section of this patent application, it has now been demonstrated that engineered E4ORF1+ endothelial cells can be used to generate a BBB-like tissue that has significantly improved barrier function (increased trans-endothelial electrical resistance ("TEEM") and decreased permeability coefficient) as compared to a BBB system comprising naïve ECs. While it was known previously that E4ORF1 expression improves EC cell survival in culture (see U.S. Pat. No. 8,465,732. See also Seandel et al. (2008), PNAS, 105(49): 19288-93), this effect of E4ORF1 on endothelial barrier function was unexpected.

In addition, and as described in more detail in the Examples section of this patent application, it has also now been found that, unlike naïve ECs, engineered E4ORF1+ ECs can be maintained long-term in direct contact with astrocytes (i.e. with no physical barrier between the two cell types) and that the barrier function of the engineered E4ORF1+ ECs is significantly improved when the cells are co-cultured with astrocytes in this way. Again, this effect of E4ORF1 on the endothelial-astrocyte interaction was unexpected.

Figure 4:
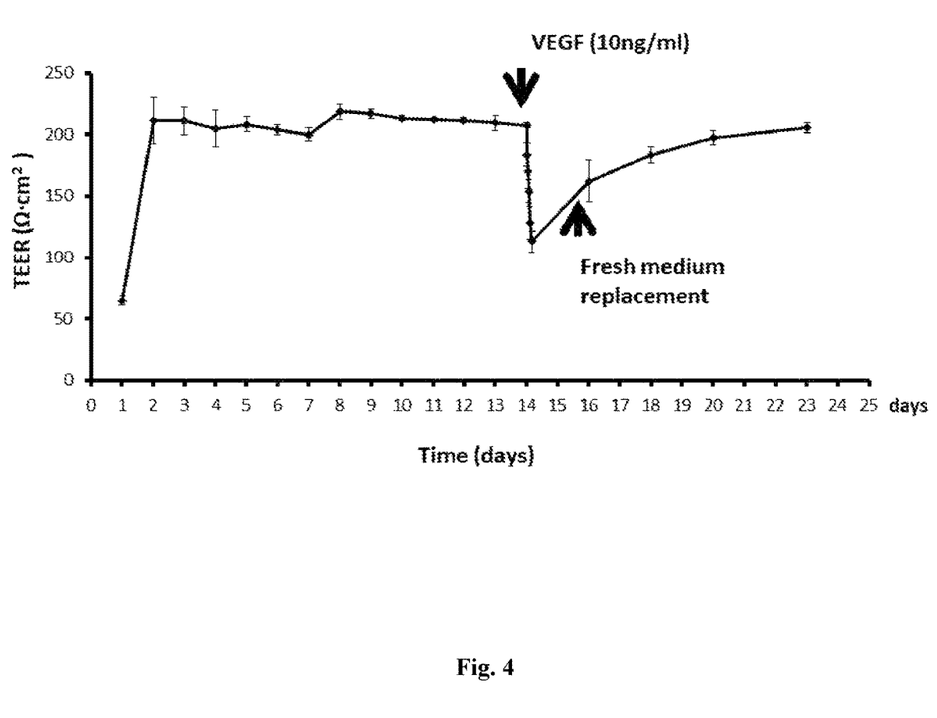

A further benefit of the use of engineered E4ORF1+ ECs instead of naïve ECs in the generation of BBB-like tissues or systems is that, unlike naïve ECs—which require serum and/or growth factors (such as VEGF) for long-term survival in culture—engineered E4ORF1+ ECs can be maintained in long-term culture (e.g. more than 1-month) even in the absence of serum and growth factors. This provides a particularly important benefit in the case of a BBB tissue/system because serum and growth factors (such as VEGF) are known to cause undesirable leakiness (i.e. reduced resistance/increased permeability) of the BBB—as confirmed in FIG. 4 of the present application.

Building on these discoveries, as well as others described in the Examples and Figures sections of this patent application, the present invention provides several new and improved BBB systems, compositions, and methods.

For example, in some embodiments the present invention provides in vitro blood-brain barrier (BBB) systems that can be useful, for example, in drug testing/screening and in studying BBB permeability and BBB function in certain disease states (e.g. cancer) or in response to injury. Thus, in one embodiment the present invention provides an in vitro blood-brain barrier (BBB) system that comprises E4ORF1+ endothelial cells. In some such embodiments the endothelial cells are mouse endothelial cells. In other embodiments the endothelial cells are human endothelial cells. In some such embodiments the endothelial cells are brain endothelial cells. In some such embodiments the in vitro BBB system also comprises a permeable solid support, which the endothelial cells will typically be disposed upon. In some such embodiments the in vitro BBB system also comprises astrocytes, which may be in direct contact with the endothelial cells.

In yet other embodiments the present invention provides screening methods for drug testing/screening and/or for studying BBB permeability and BBB function in certain disease states (e.g. cancer) or in response to injury.

In other embodiments the present invention provides compositions comprising both E4ORF1+ endothelial cells (such as E4ORF1+ brain endothelial cells) and astrocytes. In other embodiments such compositions may also comprise one or more additional cell types, including, but not limited to, pericytes and/or neural stem/progenitor cells (NSPCs). In some embodiments such compositions comprise substantially pure populations of the recited cell type, or the recited mixtures of cell types. Such compositions may be useful in a variety of situations, including in research applications and in therapeutic applications.

In yet further embodiments the present invention provides methods of treatment of defects, diseases, or disorders that affect the blood-brain barrier, such methods comprising administering E4ORF1+ endothelial cells, such as E4ORF1+ brain endothelial cells, to a living subject, such as a human subject.

These and other embodiments of the invention are described further in other sections of this patent disclosure. In addition, as will be apparent to those of skill in the art, certain modifications and combinations of the various embodiments described herein fall within the scope of the present invention.

BRIEF DESCRIPTION OF THE DRAWINGS

FIG. 5 A-B. Graphs showing permeability coefficients (Pc) of: empty trans-wells (i.e. with no cells), a monolayer of human 293T cells, naïve ECs from human brain/GBM, E4ORF1+ ECs from human kidneys, and E4ORF1+ ECs from human brain/GBM as measured using Lucifer Yellow (MW=0.4 kDa). (A) Pc data is expressed in units of cm/s. (B) Pc data is expressed as a percentage of the Pc value obtained in the empty trans-wells (i.e. with no cells). The term "VeraVec" as used in this Figure refers to E4ORF1+ ECs.

DETAILED DESCRIPTION

The "Summary of the Invention," "Figures," "Brief Description of the Figures," "Examples," and "Claims" sections of this patent disclosure describe the main embodiments of the invention. This "Detailed Description" section provides certain additional description relating to the compositions and methods of the present invention, and is intended to be read in conjunction with all other sections of this patent disclosure. Furthermore, and as will be apparent to those in the art, the different embodiments described throughout this patent disclosure can be, and are intended to be, combined in various different ways. Such combinations of the specific embodiments described herein are intended to fall within the scope of the present invention Definitions Certain definitions are provided below. Other terms are either defined elsewhere in this patent disclosure, have a meaning that is clear from the context in which they are used, or are used in accordance with their usual meaning in the art.

As used herein, the terms "about" and "approximately," when used in relation to numerical values, mean within + or −20% of the stated value.

The term "culturing" as used herein, refers to the propagation of cells on or in media of various kinds. "Co-culturing" refers to the propagation of two or more distinct types of cells on or in media of various kinds, for instance, in some embodiments, endothelial cells and astrocytes may be co-cultured.

As used herein the term "effective amount" refers to an amount of a specified agent or cell population (e.g. an E4ORF1 polypeptide, a nucleic acid molecule encoding an E4ORF1 polypeptide, or a population of E4ORF1+ engineered endothelial cells), as described herein, that is sufficient to achieve a detectable effect on one or more of the outcomes described herein. For example, in the case of expression of E4ORF1 in endothelial cells an effective amount of a nucleic acid molecule (e.g. in a vector) to be introduced/delivered to the endothelial cells may be one that results in a detectable increase in endothelial cell barrier function in a BBB model as compared to that of any suitable control (e.g. E4ORF1− endothelial cells).

In the case of methods that involve administering E4ORF1+ endothelial cells to a subject, an effective amount may be one that results in a detectable improvement of one or more desired biological or therapeutic indicators, (such as, for example, improved BBB function), as compared to that of any suitable control (e.g. E4ORF endothelial cells). An appropriate "effective amount" in any individual case may be determined empirically, for example using standard techniques known in the art, such as dose escalation studies, and may be determined taking into account such factors as the planned use, the planned mode of delivery/administration, desired frequency of delivery/administration, etc. Furthermore, an "effective amount" may be determined using assays such as those described in the Examples section of this patent disclosure to assess effects on BBB function.

The term "engineered" when used in relation to cells herein refers to cells that have been engineered by man to result in the recited phenotype (e.g. E4ORF1+), or to express a recited nucleic acid molecule or polypeptide. The term "engineered cells" is not intended to encompass naturally occurring cells, but is, instead, intended to encompass, for example, cells that comprise a recombinant nucleic acid molecule, or cells that have otherwise been altered artificially (e.g. by genetic modification), for example so that they express a polypeptide that they would not otherwise express, or so that they express a polypeptide at substantially higher levels than that observed in non-engineered endothelial cells.

As used herein the term "isolated" refers to a product, compound, or composition which is separated from at least one other product, compound, or composition with which it is associated in its naturally occurring state, whether in nature or as made synthetically.

As used herein, the term "recombinant" refers to nucleic acid molecules that are generated by man (including by a machine) using methods of molecular biology and genetic engineering (such as molecular cloning), and that comprise nucleotide sequences that would not otherwise exist in nature. Thus, recombinant nucleic acid molecules are to be distinguished from nucleic acid molecules that exist in nature—for example in the genome of an organism. A nucleic acid molecule that comprises a complementary DNA or "cDNA" copy of an mRNA sequence, without any intervening intronic sequences such as would be found in the corresponding genomic DNA sequence, would thus be considered a recombinant nucleic acid molecule. By way of example, a recombinant E4ORF1 nucleic acid molecule might comprise an E4ORF1 coding sequence operatively linked to a promoter and/or other genetic elements with which that coding sequence is not ordinarily associated in a naturally-occurring adenovirus genome.

The terms "subject" and "patient" are used herein interchangeably and refer to, except where indicated, mammals such as humans and non-human primates, as well as rabbits, rats, mice, goats, pigs, and other mammalian species.

The phrase "substantially pure" as used herein in relation to a cell population refers to a population of cells of a specified type (e.g. as determined by expression of one or more specified cell markers, morphological characteristics, or functional characteristics), or of specified types (plural) in embodiments where two or more different cell types are used together, that is at least about 50%, preferably at least about 75-80%, more preferably at least about 85-90%, and most preferably at least about 95% of the cells making up the total cell population. Thus, a "substantially pure cell population" refers to a population of cells that contain fewer than about 50%, preferably fewer than about 20-25%, more preferably fewer than about 10-15%, and most preferably fewer than about 5% of cells that are not of the specified type or types.

Nucleic Acid Molecules and Polypeptides

Several of the embodiments of the present invention described herein involve engineered endothelial cells that are E4ORF1+. E4ORF1+ cells express an adenovirus E4ORF1 polypeptide, which is encoded by an E4ORF1 nucleic acid molecule. In some embodiments the present invention involves E4ORF1 polypeptides and/or nucleic acid molecules that encode an adenovirus E4ORF1 polypeptide.

The polypeptides of the invention and the nucleic acid molecules of the invention may have amino acid sequences or nucleotide sequences that are specified herein or known in the art, or may have amino acid or nucleotide sequences that are variants, derivatives, mutants, or fragments of such amino acid or nucleotide sequences—provided that such a variants, derivatives, mutants, or fragments have, or encode a polypeptide that has, one or more of the functional properties described herein (which include, but are not limited to, those associated with BBB function).

In those embodiments involving adenovirus E4ORF1 polypeptides, the polypeptide sequence used may be from any suitable adenovirus type or strain, such as human adenovirus type 2, 3, 5, 7, 9, 11, 12, 14, 34, 35, 46, 50, or 52. In some preferred embodiments the polypeptide sequence used is from human adenovirus type 5. Amino acid sequences of such adenovirus polypeptides, and nucleic acid sequences that encode such polypeptides, are well known in the art and available in well-known publicly available databases, such as the Genbank database. For example, suitable sequences include the following: human adenovirus 9 (Genbank Accession No. CAI05991), human adenovirus 7 (Genbank Accession No. AAR89977), human adenovirus 46 (Genbank Accession No. AAX70946), human adenovirus 52 (Genbank Accession No. ABK35065), human adenovirus 34 (Genbank Accession No. AAW33508), human adenovirus 14 (Genbank Accession No. AAW33146), human adenovirus 50 (Genbank Accession No. AAW33554), human adenovirus 2 (Genbank Accession No. AP.sub.-000196), human adenovirus 12 (Genbank Accession No. AP.sub.-000141), human adenovirus 35 (Genbank Accession No. AP.sub.-000607), human adenovirus 7 (Genbank Accession No. AP.sub.-000570), human adenovirus 1 (Genbank Accession No. AP.sub.-000533), human adenovirus 11 (Genbank Accession No. AP.sub.-000474), human adenovirus 3 (Genbank Accession No. ABB 17792), and human adenovirus type 5 (Genbank accession number D12587).

In some embodiments, the polypeptides and nucleic acid molecules of the invention have the same amino acid or nucleotide sequences as those specifically recited herein or known in the art (for example in public sequence databases, such as the Genbank database). In some embodiments the polypeptides and nucleic acid molecules of the invention may have amino acid or nucleotide sequences that are variants, derivatives, mutants, or fragments of such sequences, for example variants, derivatives, mutants, or fragments having greater than 85% sequence identity to such sequences. In some embodiments, the variants, derivatives, mutants, or fragments have about an 85% identity to the known sequence, or about an 88%, 89%, 90%, 91%, 92%, 93%, 94%, 95%, 96%, 97%, 98%, or 99% sequence identity to the known sequence. In some embodiments, a variant, derivative, mutant, or fragment of a known nucleotide sequence is used that varies in length by about 50 nucleotides, or about 45 nucleotides, or about 40 nucleotides, or about 35 nucleotides, or about 30 nucleotides, or about 28 nucleotides, 26 nucleotides, 24 nucleotides, 22 nucleotides, 20 nucleotides, 18 nucleotides, 16 nucleotides, 14 nucleotides, 12 nucleotides, 10 nucleotides, 9 nucleotides, 8 nucleotides, 7 nucleotides, 6 nucleotides, 5 nucleotides, 4 nucleotides, 3 nucleotides, 2 nucleotides, or 1 nucleotide relative to the known nucleotide sequence. In some embodiments, a variant, derivative, mutant, or fragment of a known amino sequence is used that varies in length about 50 amino acids, or about 45 amino acids, or about 40 amino acids, or about 35 amino acids, or about 30 amino acids, or about 28 amino acids, 26 amino acids, 24 amino acids, 22 amino acids, 20 amino acids, 18 amino acids, 16 amino acids, 14 amino acids, 12 amino acids, 10 amino acids, 9 amino acids, 8 amino acids, 7 amino acids, 6 amino acids, 5 amino acids, 4 amino acids, 3 amino acids, 2 amino acids, or 1 amino acid relative to the known amino acid sequence.

In those embodiments where an E4ORF1 nucleic acid or amino acid sequence is used, in some embodiments such sequences are used without other sequences from the adenovirus E4 region—for example not in the context of the nucleotide sequence of the entire E4 region or not together with other polypeptides encoded by the E4 region. However, in some other embodiments such sequences may be used in conjunction with one or more other nucleic acid or amino acid sequences from the E4 region, such as E4ORF2, E4ORF3, E4ORF4, E4ORF5 or E4ORF6 sequences, or variants, mutants or fragments thereof. For example, although E4ORF1 sequences can be used in constructs (such as a viral vectors) that contain other sequences, genes, or coding regions (such as promoters, marker genes, antibiotic resistance genes, and the like), in certain embodiments, the E4ORF1 sequences are used in constructs that do not contain the entire E4 region, or that do not contain other ORFs from the entire E4 region, such as E4ORF2, E4ORF3, E4ORF4, E4ORF5 and/or E4ORF6.

The nucleic acid molecules of the invention can be used in constructs that contain various other nucleic acid sequences, genes, or coding regions, depending on the desired use, for example, antibiotic resistance genes, reporter genes or expression tags (such as, for example nucleotides sequences encoding GFP), or any other nucleotide sequences or genes that might be desirable. The polypeptides of the invention can be expressed alone or as part of fusion proteins.

In some embodiments nucleic acid molecules of the invention can be under the control of one or more promoters to allow for expression. Any promoter able to drive expression of the nucleic acid sequences in the desired cell type can be used. Examples of suitable promoters include, but are not limited to, the CMV, SV40, RSV, HIV-Ltr, and MML promoters. The promoter can also be a promoter from the adenovirus genome, or a variant thereof. For example, where E4ORF1 is used, the promoter can be the promoter used to drive expression of corresponding genes in an adenovirus.

In some embodiments, nucleic acid molecules of the invention can be placed under the control of an inducible promoter, so that expression of the nucleic acid sequences can be turned on or off as desired. Any suitable inducible expression system can be used, such as, for example, a tetracycline inducible expression system, or a hormone inducible expression system. For example, the nucleic acid molecules of the invention can be expressed while they are needed and then switched off when the desired outcome has been achieved, for example when there has been sufficient growth or proliferation of the endothelial cells. The ability to turn on or turn off expression could be particularly useful for in vivo applications.

The nucleic acid molecules of the invention may comprise naturally occurring nucleotides, synthetic nucleotides, or a combination thereof. For example, in some embodiments the nucleic acid molecules of the invention can comprise RNA, such as synthetic modified RNA that is stable within cells and can be used to direct protein expression/production directly within cells. In other embodiments the nucleic acid molecules of the invention can comprise DNA. In embodiments where DNA is used, the DNA sequences may be operably linked to one or more suitable promoters and/or regulatory elements to allow (and/or facilitate, enhance, or regulate) expression within cells, and may be present in one or more suitable vectors or constructs. The nucleic acid molecules of the invention can be introduced into endothelial cells in the same nucleic acid construct or they can be introduced in separate nucleic acid constructs.

The nucleic acid molecules of the invention can be introduced into endothelial cells using any suitable system known in the art, including, but not limited to, transfection techniques and viral-mediated transduction techniques. Transfection methods that can be used in accordance with the present invention include, but are not limited to, liposome-mediated transfection, polybrene-mediated transfection, DEAE dextran-mediated transfection, electroporation, calcium phosphate precipitation, microinjection, and microparticle bombardment. Viral-mediated transduction methods that can be used include, but are not limited to, lentivirus-mediated transduction, adenovirus-mediated transduction, retrovirus-mediated transduction, adeno-associated virus-mediated transduction and herpesvirus-mediated transduction.

The present invention also provides vectors, including expression vectors that contain nucleic acid molecules of the invention. For example, in one embodiment, the present invention provides an expression vector comprising a nucleotide sequence encoding an E4ORF1 polypeptide. In some such embodiments the expression vector is a lentivirus vector.

In some embodiments a peptidomimetic may be used. A peptidomimetic is a small protein-like chain designed to mimic a polypeptide. Such a molecule could be designed to mimic any of the polypeptides of the invention (e.g. an E4ORF1 polypeptide). Various different ways of modifying a peptide to create a peptidomimetic or otherwise designing a peptidomimetic are known in the art and can be used to create a peptidomimetic of one of the polypeptides of the invention.

The handling, manipulation, and expression of the polypeptides and nucleic acid molecules of the invention may be performed using conventional techniques of molecular biology and cell biology. Such techniques are well known in the art. For example, one may refer to the teachings of Sambrook, Fritsch and Maniatis eds., "Molecular Cloning A Laboratory Manual, 2nd Ed., Cold Springs Harbor Laboratory Press, 1989); the series Methods of Enzymology (Academic Press, Inc.), or any other standard texts for guidance on suitable techniques to use in handling, manipulating, and expressing nucleotide and/or amino acid sequences. Additional aspects relevant to the handling or expression of E4ORF1 sequences are described in U.S. Pat. No. 8,465,732, the contents of which are hereby incorporated by reference.

Endothelial Cells

In some embodiments the present invention provides engineered endothelial cells, such as E4ORF1+ engineered endothelial cells. The engineered endothelial cells can be derived from any suitable source of endothelial cells known in the art. For example, in some embodiments the endothelial cells are vascular endothelial cells. In some embodiments the endothelial cells are primary endothelial cells. In some embodiments the engineered endothelial cells are mammalian cells, such as human or non-human primate cells, or rabbit, rat, mouse, goat, pig, or other mammalian cells. In some embodiments the endothelial cells are primary human endothelial cells. In some embodiments the endothelial cells are umbilical vein endothelial cells (UVECs), such as human umbilical vein endothelial cells (HUVECs). Other suitable endothelial cells that can be used include those described previously as being suitable for E4ORF1-expression in U.S. Pat. No. 8,465,732, the contents of which are hereby incorporated by reference. In preferred embodiments the endothelial cells are brain endothelial cells, such as brain microvascular endothelial cells.

In some embodiments the engineered endothelial cells are gene-modified such that they comprise one or more genetic modifications in addition to and apart from the expression of the specific recited molecules (e.g. E4ORF1). For example, such cells may comprise a corrected version of a gene known to be involved in, or suspected of being involved in, a disease or disorder that affects endothelial cells or that affects BBB function, or any other gene, such as a therapeutically useful gene, that it may be desired to provide in endothelial cells or administer or deliver using engineered endothelial cells.

The engineered endothelial cells of the invention may exist in, or be provided in, various forms. For example, in some embodiments the engineered endothelial cells may comprise a population of cells, such as an isolated population of cells. In some embodiments the engineered endothelial cells may comprise a population of cells in vitro. In some embodiments the engineered endothelial cells may comprise a substantially pure population of cells. For example, in some embodiments at least about 50%, preferably at least about 75-80%, more preferably at least about 85-90%, and most preferably at least about 95% of the cells making up a total cell population will be engineered endothelial cells of the invention. In some embodiments the engineered endothelial cells may be provided in the form of a composition containing the engineered cells and one or more additional components. For example, in some embodiments the present invention may provide a composition comprising a population of engineered endothelial cells as described herein together with a carrier solution, such as a physiological saline solution, cell suspension medium, cell culture medium, or the like. In some embodiments such compositions may be therapeutic compositions—comprising a population of engineered endothelial cells and a carrier solution that is suitable for administration to a subject, such as a human subject. Other therapeutically acceptable agents can be included if desired. One of ordinary skill in the art can readily select suitable agents to be included in the therapeutic compositions depending on the intended use.

In some embodiments the engineered endothelial cells of the invention may be provided in the form of a composition (e.g. a therapeutic composition) that contains the engineered endothelial cells of the invention and one or more additional cell types. Such additional cell types may be, for example, cell types that can be maintained, cultured, or expanded in the presence of the engineered endothelial cells (e.g. using the engineered endothelial cells of the invention as "feeder" cells), or any other cell type for which it may be desired to use together with the engineered endothelial cells of the invention—for example for use in an in vitro model system or for use in co-administration to a subject. In some preferred embodiments the engineered endothelial cells of the invention may be provided in a composition (e.g. a therapeutic composition) that contains both the engineered endothelial cells of the invention and astrocytes.

Astrocytes

Several of the embodiments of the present invention involve astrocytes. Any suitable astrocytes can be used. In some embodiments the astrocytes are mouse astrocytes. In some embodiments they are human astrocytes. The astrocytes may be primary astrocytes (e.g. isolated from CNS tissue) or they may be cultured astrocyte lines. Methods for obtaining and culturing astrocytes are known in the art and any such methods can be used in conjunction with the present invention.

Model Systems, Methods, and Applications

In some embodiments the present invention provides BBB model systems, compositions and kits useful in such systems, and screening methods that utilize such BBB model systems. The use of BBB model systems for drug screening and/or for biological research is known in the art, and the novel BBB model systems of the present invention can be utilized in the same or similar ways to those systems that are known in the art. For example, E4ORF1+ endothelial cells can be used in place of the naïve (non-E4ORF1+) endothelial cells typically used in other BBB model systems. Typically such systems will comprise a confluent endothelial cell monolayer grown on a solid permeable support such that the endothelial cells form a barrier that physically separates two chambers on either side of the endothelial cell layer. In this way, one can study the ability of agents to cross from one physical compartment to the other physical compartment through the endothelial cell barrier.

As mentioned above, such BBB model systems may be used in drug screening. For example, in some embodiments the present invention provides methods for assessing the blood-brain barrier permeability of a candidate agent, where such methods comprise contacting E4ORF1+ endothelial cells in a BBB model system with one or more candidate agents. Similarly, in some embodiments the present invention provides methods for assessing the effect of one or more candidate agents on the permeability of the blood-brain barrier, where such methods comprise contacting E4ORF1+ endothelial cells in a BBB model system with one or more candidate agents. Similarly, in some embodiments the present invention provides methods for assessing effect of one or more test cell types on the permeability of the blood-brain barrier, where such methods comprise including one or more test cell types in an E4ORF1+ endothelial cell-containing BBB model system as described herein and testing the effects of that test cell type on BBB barrier function and permeability. Additional details of each of such screening/testing methods (including suitable assays for assessing BBB barrier function and permeability) are described elsewhere in this patent application—including in the Examples and Claims.

In some embodiments, the present invention provides various therapeutic methods, such as methods for treating subjects in need thereof by administering to such subjects an effective amount of the engineered endothelial cells of the invention (or of a composition comprising such engineered endothelial cells). In such treatment methods, the cells can be administered to subjects using any suitable means known in the art. For example, the cells can be administered by injection or infusion into the blood stream or tissue at a desired location. For example, in the case of treatment of diseases, disorders, or conditions of the CNS, engineered cells according to the present invention may be administered directly into, or in the vicinity of, the affected areas of the brain or spinal cord. In some embodiments the engineered endothelial cells may be administered together with one or more additional cell types. Such additional cell types may be, for example, astrocytes. The engineered endothelial cells can be administered in a single dose or in multiple doses. The skilled artisan will be able to select a suitable method of administration according and a suitable dosing regimen depending on the desired use.

In some embodiments engineered endothelial cells of the present invention can be created in vivo, for example for research purposes or for therapeutic applications. For example, in some aspects, the present invention provides various therapeutic methods, such as methods for treating subjects in need thereof, which comprise administering to such subjects an effective amount of a nucleic acid molecule that encodes an E4ORF1 polypeptide (for example in a suitable vector, and/or under the control of a suitable promoter) such that endothelial cells in the subject are transfected or transduced with such nucleic acid molecules and become engineered endothelial cells in vivo. In such methods, the nucleotide molecules can be administered to subjects using any suitable means known in the art. For example, the nucleotide molecules (for example in a suitable vector) can be administered by injection or infusion into the blood stream or tissue at a desired location. The nucleic acid molecules can be administered in a single dose or in multiple doses. The skilled artisan will be able to select a suitable method of administration according and a suitable dosing regimen depending on the desired use.

In some embodiments the engineered endothelial cells of the invention are mitotically inactivated prior to use (e.g. therapeutic use) such that they cannot replicate. This can be achieved, for example, by using a chemical agent such as mitomycon C or by irradiating the engineered endothelial cells.

Cell Culture Methods

Methods of culturing cells are well known in the art and any suitable cell culture methods can be used. For example, the engineered endothelial cells of the invention can be cultured using methods known to be useful for culturing other endothelial cells, or, methods known to be useful for culturing E4ORF1-expressing endothelial cells, for example as described in U.S. Pat. No. 8,465,732, the contents of which are hereby incorporated by reference. In some embodiments the engineered endothelial cells of the invention can be cultured in the absence of serum, or in the absence of exogenous growth factors, or in the absence of both serum and exogenous growth factors. The engineered endothelial cells of the invention can also be cryopreserved. Various methods for cell culture and cell cryopreservation are known to those skilled in the art, such as the methods described in Culture of Animal Cells: A Manual of Basic Technique, 4th Edition (2000) by R. Ian Freshney ("Freshney"), the contents of which are hereby incorporated by reference.

In some embodiments the present invention provides co-culture methods, for example involving co-culture of E4ORF1+ endothelial cells and astrocytes. Such co-culture methods may comprise culturing E4ORF1+ endothelial cells and astrocytes together in the same culture vessel. In some embodiments the E4ORF1+ endothelial cells and the astrocytes may be in direct cell-to-cell contact (without any barrier e.g. membrane separating the E4ORF1+ endothelial cells from the astrocytes). In some such embodiments the engineered endothelial cells may form a confluent monolayer on a surface of a culture vessel or some other solid but permeable substrate, and the astrocytes may be placed on the endothelial cell monolayer.

Kits

The present invention also provides kits for making the BBB model systems of the invention and/or for making, using, or performing any of the compositions or methods described herein. Such kits may contain any of the components described herein, including, but not limited to, nucleotide sequences (for example in a vector), engineered endothelial cells, astrocytes, media or compositions useful for maintaining or expanding the engineered endothelial cells or astrocytes, solid permeable supports for culture of endothelial cell monolayers, or any combination thereof. All such kits may optionally comprise instructions for use, containers, culture vessels and the like. A label may accompany the kit and may include any writing or recorded material, which may be electronic or computer readable form (e.g., disk, optical disc, memory chip, or tape) providing instructions or other information for use of the kit contents.

Certain aspects of the present invention are further described in the following non-limiting Example.

EXAMPLE

Mouse Brain Microvascular Endothelial Cell Isolation and Culture

Five to eight three-week old mice were sacrificed, and the brains were isolated into dissection medium. The two cerebral hemispheres were tweezed apart and the meninges and the olfactory bulbs were carefully removed. Fine scissors were used to mince the tissues into small pieces (about 0.5 mm diameter). The small tissue pieces were collected and transferred with the dissection medium into a 15 ml conical tube. The tissue pieces were allowed to settle for approximately 1-2 minutes, and were then removed from the dissection medium carefully. 6-8 ml of TrypLE was added to the conical tube and the cap closed tightly. The tube was flipped up and down 3 times followed by placing the tube in a water bath at 37° C. for 15 minutes, while swirling the tube occasionally. The TrypLE was then removed without disturbing the diced tissue and 1-2 ml of mouse endothelia medium (http://angiocrinebioscience.com/wp-content/uploads/VeraVec-Mouse-Brain-Instruction-Sheet.pdf) was added. DNAse was added for 1 minute while agitating the tube by frequent tapping. The tissue pieces were then rinsed with mouse endothelia medium 3 times. The tissue pieces were then triturated in approximately 1 ml of mouse endothelia medium by passing the tissue pieces and medium up and down 10 times, followed by triturating the tissue and medium once using a flame polished glass pipette. The triturated cell suspension was then centrifuged for 5 minutes at 400 g and the supernatant was then removed. The cell pellet was re-suspended with complete mouse endothelial medium and plated into T75 flasks coated with fibronectin. The medium was replaced with fresh mouse endothelial medium every other day until the culture reached confluence. CD31 antibody was used to purify the brain microvascular endothelial cells by fluorescence activated cell sorting (FACS). Cells obtained following sorting were replated on fibronectin coated wells (6-well plate), with approximately 400,000 cells per well. The next day, the cells were transduced with E4ORF1 lentivirus (40-50 µl concentrated virus) using polybrene (8 µg/ml, medium without antibiotics). After 24 hours the infection medium was replaced with regular mouse endothelial medium. The cells were passaged upon reaching confluence.

Human Brain Microvascular Endothelial Cell Isolation and Culture

Human brain tissue was obtained by surgical removal from patients with epilepsy, or from patients with glioblastoma (GBM). The human tissue was then processed and cultured as described above for mouse tissue.

Trans-Endothelial Electrical Resistance (TEER) and Lucifer Yellow Permeability Assays On day 0 endothelial cells were plated into transwell inserts (Corning Inc., 353180) that fit 12-well plates. The cells reached confluence by the following day (approximately 200,000-400,000 cells/insert). Daily measurements of trans-endothelial electrical resistance ("TEER") commenced on day 1. The medium was replaced with "TEER booster" medium containing hydrocortisone, cAMP, PKA, phosphodiesterase inhibitor, retinoic acid, insulin, transferrin, and sodium selenite. For astrocyte co-culture experiments, on day 2 (after a monolayer of ECs had formed in the transwell inserts) astrocytes were added to the transwell inserts at a density of 50,000 cells per insert such that the astrocytes were in direct contact with the endothelial cells. For GBM cell co-culture experiments, GBM cells were added to the bottom of the wells holding the transwell inserts (with EC monolayers) on day 4.

For lucifer yellow (LY) based permeability assays, the following protocol was was performed. On day 1 cells were plated into inserts that fit 12-well plates such that they reached confluence by the next day. (~200,000-400,000 cells/insert). On day 2 the medium was replaced with "TEER booster" medium containing hydrocortisone, cAMP, PKA, phosphodiesterase inhibitor, retinoic acid, insulin, transferrin, and sodium selenite. On day 3 the medium was replaced with serum free "TEER booster" medium (Neural progenitor medium with N2 and B27). On day 4 TEER measurements were made prior to performing the LY-based permeability assay. The LY assay was performed using a commercially available assay essentially as per the manufacturer's instructions (http://ebiotrade.com/buyf/productsf/BD %20Falcon/insert_protocol_lucifer_yellow_permeability_assay.pdf). The LY assay was used as per the manufacturer's instructions to determine the permeability coefficient or "Pc" (cm/second). The Pc=(V/(A×Ci))×(Cf/T), where V is the volume of the basal chamber (mL), A is the area of the membrane insert (cm$^2$), Ci is the initial concentration of LY, Cf is the final concentration of LY, and T is the assay time in seconds (T was 1 hour (3600 seconds) and/or 4 hours). The Pc value calculated using this system provides a quantitative measure of barrier integrity and function. In general, a Pc<$2.5 \times 10^{-6}$ cm/s in a Lucifer yellow-based assay indicates a BBB-quality barrier function.

Immunocytochemistry

Monolayers of E4ORF1+ mouse brain endothelial cells (ECs) were fixed with 4% paraformaldehyde before performing immunohistochemistry using antibodies specific for Claudin 5 and MFSD2A.

Results

Figure 1:
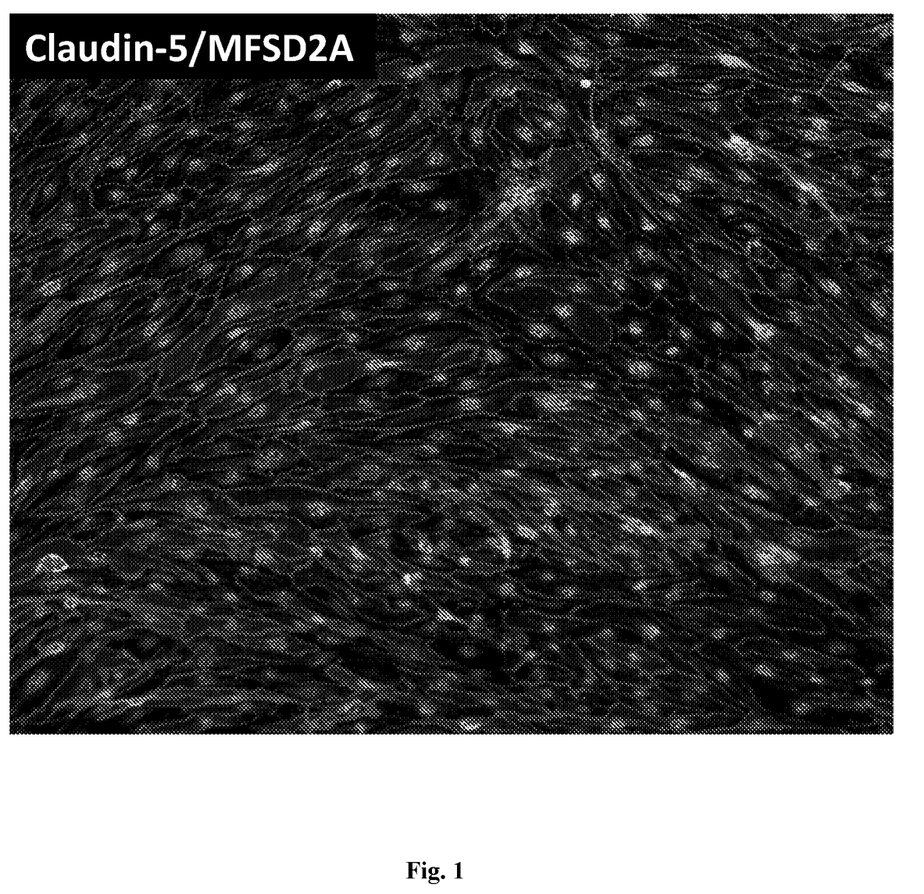
FIG. 1. Fluorescence micrograph showing immunohistochemical staining of a monolayer of E4ORF1+ mouse brain endothelial cells (ECs) (derived from 3-week old murine cortex). Cells were labelled using primary antibodies specific for the tight junction marker Claudin 5 and the CNS-specific EC marker MFSD2A and fluorescently-labeled secondary antibodies. Claudin-5 protein was detected at the cell borders, while MFSD2A protein was detected intracellularly. The endothelial cells were derived from the cortex of 3-week old mice.

E4ORF1+ mouse brain endothelial cell monolayers were found to express both the tight junction marker Claudin 5 and the CNS-specific EC MFSD2A (see FIG. 1).

Figure 2A:
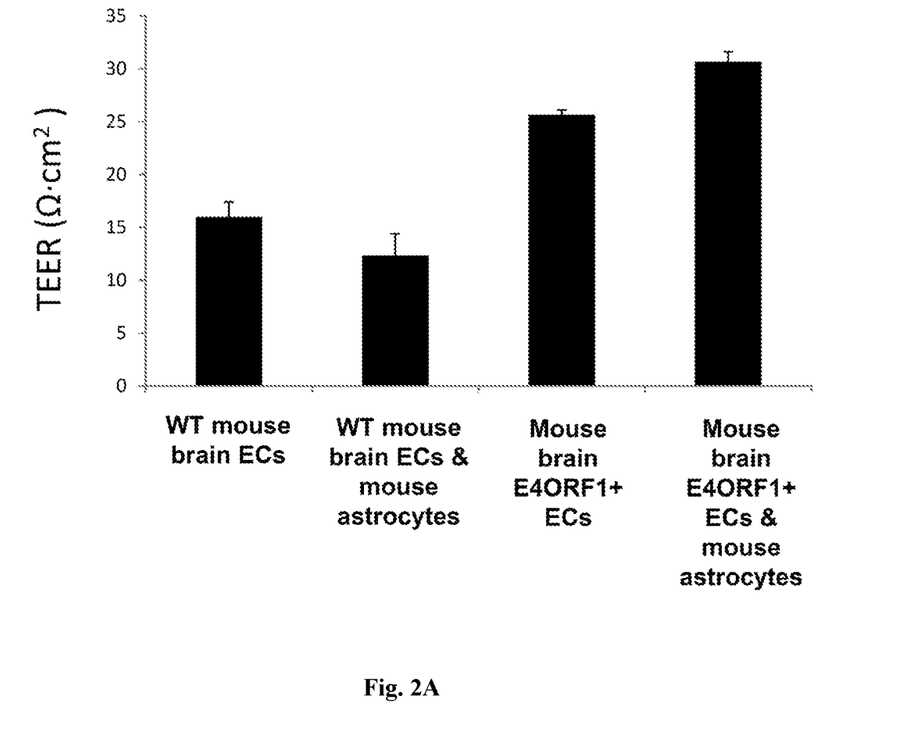
FIG. 2A-B. (A) Graph showing TEER measurements in $\Omega \cdot cm^2$ as recorded from monolayer cultures of: wild-type (WT) mouse brain ECs, WT mouse brain ECs co-cultured with mouse astrocytes, E4ORF1+ mouse brain ECs, and E4ORF1+ mouse brain ECs co-cultured with mouse astrocytes. TEER values were measured after 3 days in culture. As used herein "WT" refers to ECs that have not been engineered to express E4ORF1. (B) Graph showing TEER measurements as recorded from monolayer cultures of: E4ORF1+ mouse brain ECs and E4ORF1+ mouse brain ECs co-cultured with mouse astrocytes. TEER values were measured after 3 days in culture. TEER measurements are expressed as a percentage of the TEER value obtained in the absence of astrocyte co-culture. An approximately 20% increase in TEER value was observed when of E4ORF1+ ECs were co-cultured with astrocytes in a direct contact fashion.
Figure 2B:
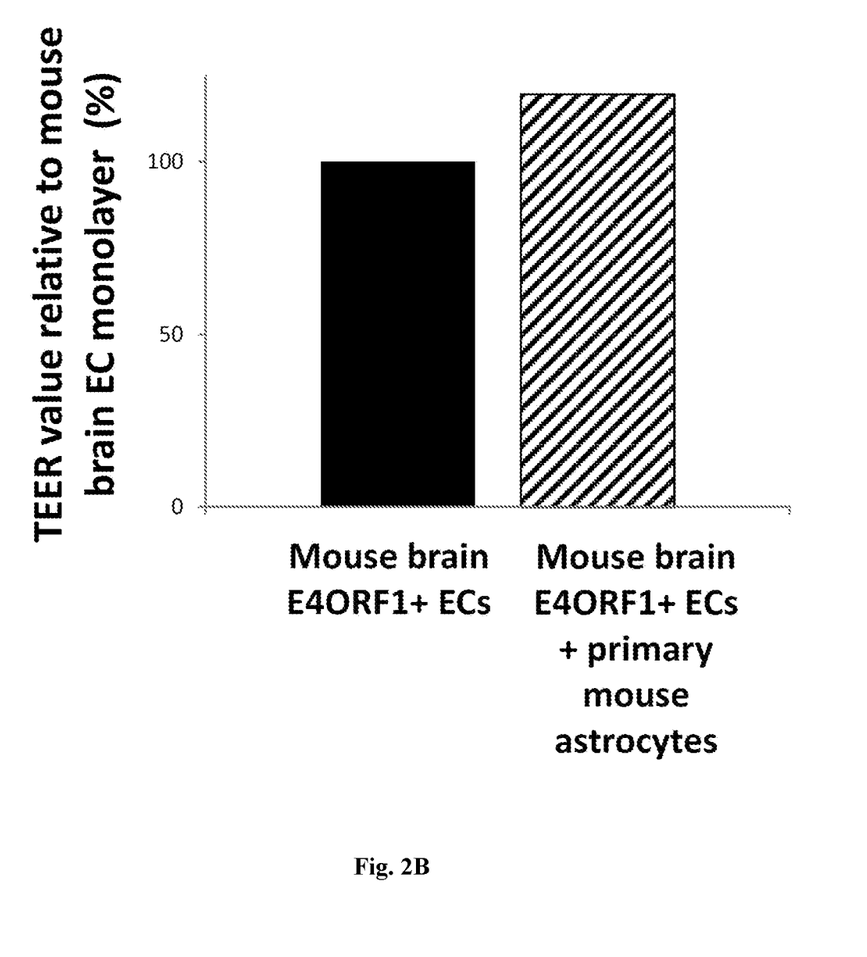

Expression of E4ORF1 in mouse brain endothelial cells was found to increase TEER values as compared to those observed in naïve (not E4ORF1+) mouse brain ECs, and co-culture of the E4ORF1+ mouse brain endothelial cells with astrocytes increased TEER values/barrier function still further (see FIGS. 2A and 2B—TEER measurements on day 3 of culture). Astrocytes were able to form a monolayer in direct contact with the E4ORF1+ ECs, while when naïve (non-E4ORF1+) ECs were used the astrocytes formed "islands" of astrocytes in a "sea" of ECs (as opposed to forming the multilayered astrocyte/EC structure observed when E4ORF1+ ECs were used) and TEER values (indicative of barrier function) were lower when astrocytes were cultured with naïve (non-E4ORF1+) ECs as opposed to E4ORF1+ ECs (see FIG. 2A).

Figure 3:
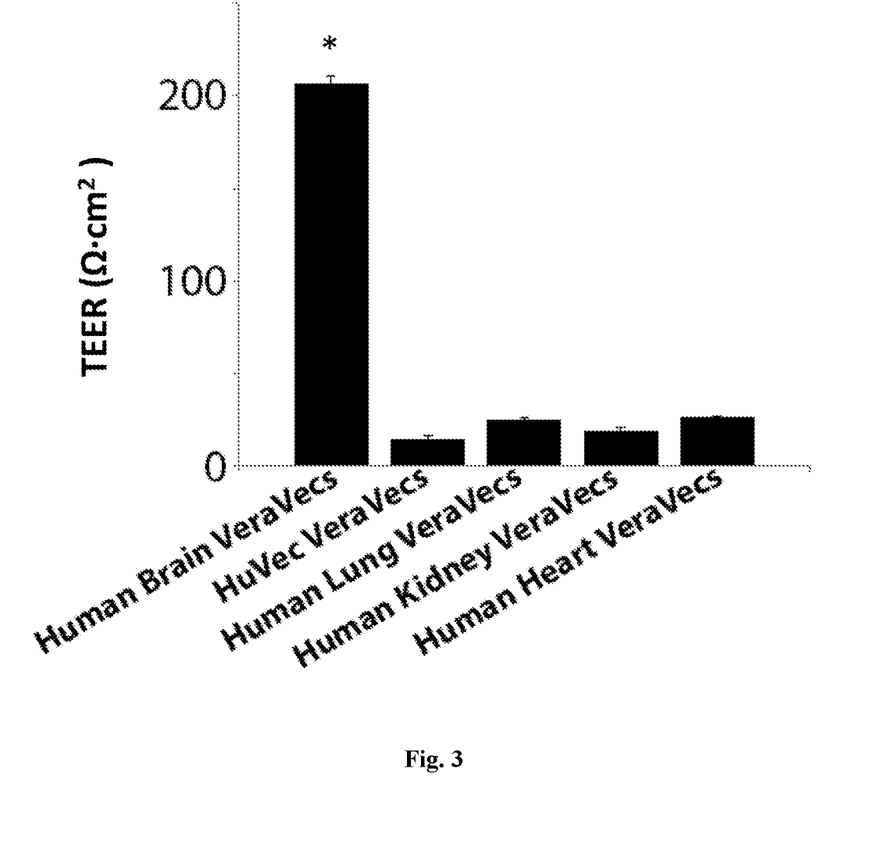
FIG. 3. Graph showing TEER measurements in $\Omega \cdot cm^2$ as recorded from monolayer cultures of E4ORF1+ ECs derived from human brain, human umbilical cord vein ("HuVec"), human lung, human kidney, or human heart. The term "VeraVec" as used in this Figure refers to E4ORF1+ ECs. TEER values were measured after 3 days in culture FIG. 4. Graph showing TEER measurements in $\Omega \cdot cm^2$ as recorded from a monolayer culture of E4ORF1+ human brain ECs over a period of around 24 days. Arrows indicate the time point at which VEGF was added to the culture and the time point the VEGF-containing medium was replaced with fresh medium not containing VEGF.

As shown in FIG. 3, human brain E4ORF1+ endothelial cells manifested a uniquely high TEER value (~200 Ω·cm2 on day 2) as compared to E4ORF1+ ECs derived from human umbilical cord, lung, kidney or heart (~25 Ω·cm2). (Note—in FIG. 3 the term "VeraVec" refers to E4ORF1+ ECs.) Furthermore, TEER values of the human brain E4ORF1+ brain endothelial cell monolayers remained high (around 200 Ω·cm2) for 6 weeks. Additionally, permeability of the human brain E4ORF1+ brain endothelial cell monolayers was shown to be responsive to extracellular stimuli known affect BBB permeability—such as VEGF (see FIG. 4).

Figure 5A:
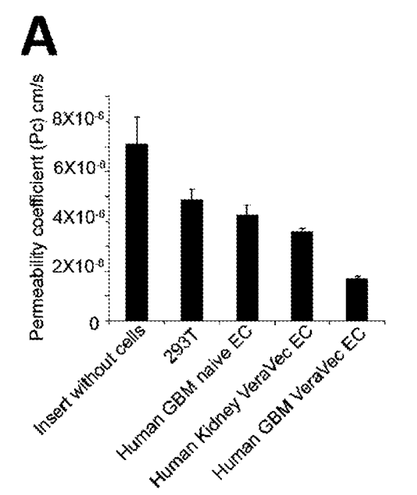
Figure 5B:
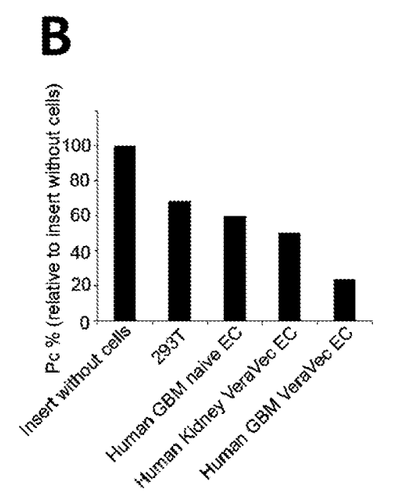

FIG. 5 shows the results of an experiment in which human E4ORF1+ brain endothelial cells were compared to naïve (non-E4ORF1-expressing) human brain endothelial cells, human E4ORF1+ kidney endothelial cells, human 293T cells, and empty trans-wells (i.e. with no cells) in assays to measure TEER values and determine permeability coefficients (Pc). (Note—in FIG. 5 the term "VeraVec" refers to E4ORF1+ cells.) The Pc and TEER values obtained were as follows: (a) insert without cells –Pc=7.11±1.07×$10^{-6}$ cm/s; TEER=0; (b) 293T cells—Pc=4.86±0.44×$10^{-6}$ cm/s, TEER=~5 Ω·cm$^2$, (c) naïve human GBM ECs–Pc=4.26±0.40×$10^{-6}$ cm/s, TEER=~50 Ω·cm$^{2'}$ (d) E4ORF1+ human kidney ECs–Pc=3.57±0.13×$10^{-6}$ cm/s, TEER=~35 Ω·cm$^2$, and (e) E4ORF1+ human GBM ECs–Pc=1.69±0.12×$10^{-6}$ cm/s, TEER=~120 Ω·cm$^2$. The human E4ORF1+ brain endothelial cells exhibited the lowest Pc value—i.e. the best barrier function.

Figure 6:
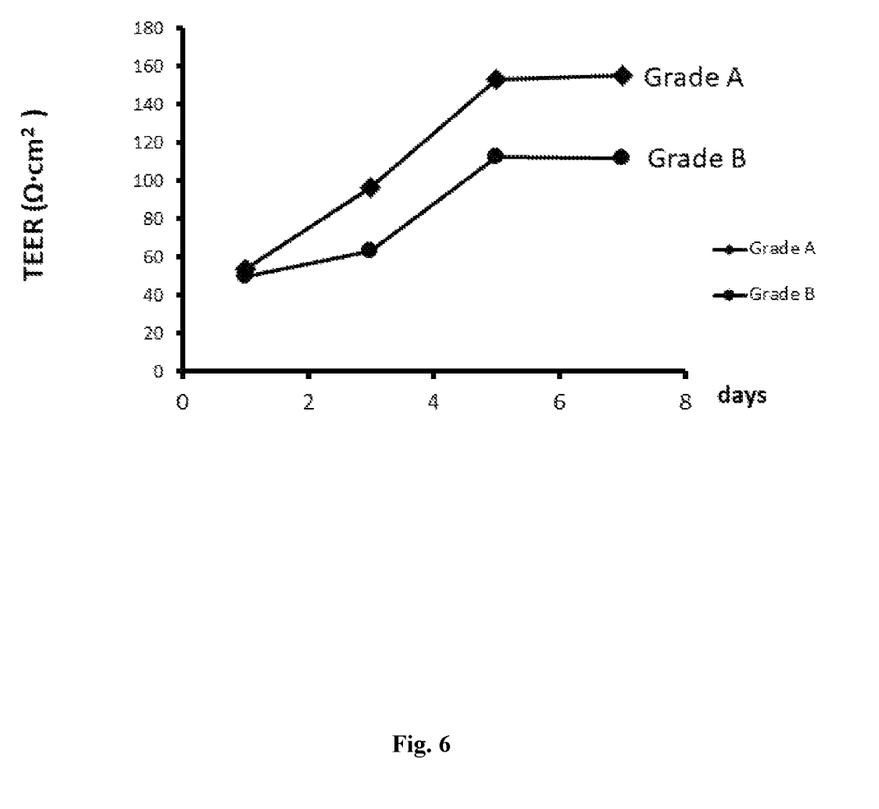
FIG. 6. Graph showing TEER measurements in $\Omega \cdot cm^2$ recorded over a period of around 8 days in monolayer cultures of E4ORF1+ human brain ECs derived from Grade A and Grade B GBMs.

In another experiment human E4ORF1+ brain endothelial cells were generated from two different GBM samples—one obtained from the center/core of the tumor (referred to as Grade B), and the other obtained from the periphery of the tumor in the region adjacent to normal tissue (referred to as Grade A). As shown in FIG. 6, a significant difference in the TEER values between the Grade A and Grade B E4ORF1+ brain endothelial cells was observed.

Figure 7:
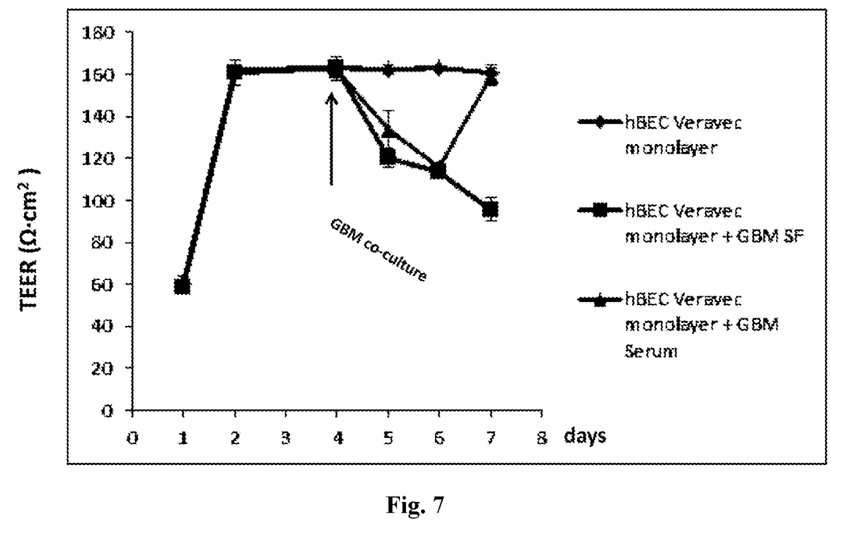
FIG. 7. Graph showing TEER measurements in $\Omega \cdot cm^2$ recorded over a period of around 8 days in 3 different monolayer cultures of E4ORF1+ human brain ECs. On day 4 GBM tumor cells were added to 2 of the 3 cultures ("+ GBM")—as indicated. Of the two EC/GBM co-cultures, one was maintained in serum free conditions ("SF") and the other was cultured in the presence of serum—as indicated. The term "VeraVec" as used in this Figure refers to E4ORF1+ ECs.

FIG. 7 shows the results of an experiment in which human E4ORF1+ brain endothelial cells derived from patients with epilepsy were co-cultured with human GBM tumor cells. TEER values dropped upon GBM tumor cell co-culture. When the co-culture was performed the absence of serum the TEER values dropped to about 50% of the value observed when the E4ORF1+ brain endothelial cells were cultured alone—without GBM tumor cells. When the co-culture was performed in the presence of fetal bovine serum (FBS) TEER values declined for two days but recovered on the third day of co-culture. We hypothesized that this recovery may have been due to a differentiation of the GBM cells induced by the FBS treatment.

These results show that the model system of the present invention exhibits many of the key functional properties of the BBB—including, but not limited to, providing a high-resistance barrier the permeability of which is responsive to a variety of environmental cues.

The present invention is further described by the following claims.

We claim:

1. An in vitro blood-brain barrier (BBB) system comprising: (a) a confluent monolayer of endothelial cells that express an adenovirus E4ORF1 polypeptide and (b) astrocytes in direct contact with the monolayer of endothelial cells.

2. The system of claim 1, wherein the endothelial cells are brain endothelial cells.

3. The system of claim 1, wherein the endothelial cells are human endothelial cells.

4. The system of claim 1, wherein the astrocytes are human astrocytes.

5. The system of claim 1, wherein the endothelial cells are disposed upon a permeable solid support.

6. The system of claim 2, wherein the endothelial cells are disposed upon a permeable solid support.

7. The system according to claim 1, wherein the endothelial cell monolayer has a trans endothelial electrical resistance (TEER) of greater than about 25 $\Omega \cdot cm^2$.

8. The system according to claim 1, wherein the endothelial cell monolayer has a trans endothelial electrical resistance (TEER) of greater than about 50 $\Omega \cdot cm^2$.

9. The system according to claim 1, wherein the endothelial cell monolayer has a trans endothelial electrical resistance (TEER) of greater than or greater than about 100 $\Omega \cdot cm^2$.

10. The system according to claim 2, wherein the endothelial cell monolayer has a trans endothelial electrical resistance (TEER) of greater than about 25 $\Omega \cdot cm^2$.

11. The system according to claim 2, wherein the endothelial cell monolayer has a trans endothelial electrical resistance (TEER) of greater than about 50 $\Omega \cdot cm^2$.

12. The system according to claim 2, wherein the endothelial cell monolayer has a trans endothelial electrical resistance (TEER) of greater than or greater than about 100 $\Omega \cdot cm^2$.

13. The system according to claim 1, wherein the endothelial cell monolayer has a Lucifer Yellow permeability coefficient (Pc) of less than about $2.5 \times 10^{-6}$ cm/s.

14. The system according to claim 2, wherein the endothelial cell monolayer has a Lucifer Yellow permeability coefficient (Pc) of less than about $2.5 \times 10^{-6}$ cm/s.

15. A method for assessing the blood-brain barrier permeability of a candidate agent, the method comprising: (a) contacting one side of the endothelial cell monolayer in a BBB system according to claim 1 with a candidate agent, and (b) determining whether the candidate agent is present on the other side of the endothelial cell monolayer, wherein if the candidate agent is present on the other side of the endothelial cell monolayer the agent is blood-brain-barrier permeable, and wherein if the candidate agent is not present on the other side of the endothelial cell monolayer the agent is not blood-brain-barrier permeable.

16. A method for assessing the effect of an agent on the permeability of the blood-brain barrier, the method comprising: (a) contacting the endothelial cells in a BBB system according to claim 1 with a candidate agent, and (b) determining the trans endothelial electrical resistance (TEER) of the BBB system, wherein if the candidate agent decreases the TEER of the BBB system as compared to the TEER in the absence of the candidate agent, then the candidate agent increases the permeability of the BBB, and if the candidate agent increases the TEER of the BBB system as compared to the TEER in the absence of the candidate agent, then the candidate agent reduces the permeability of the BBB.

17. A method for assessing the effect of an agent on the permeability of the blood-brain barrier, the method comprising: contacting the endothelial cells in a BBB system according to claim 1 with a candidate agent, and determining the permeability coefficient (Pc) of the BBB system, wherein if the candidate agent decreases the Pc of the BBB system as compared to the Pc in the absence of the candidate agent, then the candidate agent decreases the permeability of the BBB, and if the candidate agent increases the Pc of the BBB system as compared to the Pc in the absence of the candidate agent, then the candidate agent increases the permeability of the BBB.

18. A method for assessing the blood-brain barrier permeability of a candidate agent, the method comprising: (a) contacting one side of an endothelial cell monolayer in a BBB system according to claim 2 with a candidate agent, and (b) determining whether the candidate agent is present on the other side of the endothelial cell monolayer, wherein if the candidate agent is present on the other side of the endothelial cell monolayer the agent is blood-brain-barrier permeable, and wherein if the candidate agent is not present on the other side of the endothelial cell monolayer the agent is not blood-brain-barrier permeable.

19. A method for assessing the effect of an agent on the permeability of the blood-brain barrier, the method comprising: (a) contacting the endothelial cells in a BBB system according to claim 2 with a candidate agent, and (b) determining the trans endothelial electrical resistance (TEER) of the BBB system, wherein if the candidate agent decreases the TEER of the BBB system as compared to the TEER in the absence of the candidate agent, then the candidate agent increases the permeability of the BBB, and if the candidate agent increases the TEER of the BBB system as compared to the TEER in the absence of the candidate agent, then the candidate agent reduces the permeability of the BBB.

20. A method for assessing the effect of an agent on the permeability of the blood-brain barrier, the method comprising: contacting the endothelial cells in a BBB system according to claim 2 with a candidate agent, and determining the permeability coefficient (Pc) of the BBB system, wherein if the candidate agent decreases the Pc of the BBB system as compared to the Pc in the absence of the candidate agent, then the candidate agent decreases the permeability of the BBB, and if the candidate agent increases the Pc of the BBB system as compared to the Pc in the absence of the candidate agent, then the candidate agent increases the permeability of the BBB.

* * * * *